United States Patent [19]

Horne

[11] 3,998,594

[45] Dec. 21, 1976

[54] CUVETTE FOR AUTOMATIC CHEMICAL TESTING APPARATUS

[75] Inventor: Thomas Horne, Leighton Buzzard, England

[73] Assignee: Coulter Electronics, Inc.

[22] Filed: Nov. 26, 1975

[21] Appl. No.: 635,438

[30] Foreign Application Priority Data

Oct. 3, 1975   United Kingdom ............ 40673/75

[52] U.S. Cl. .............................. 23/259; 23/253 R; 356/246
[51] Int. Cl.² .................. G01N 33/16; G01N 1/10; G01N 23/10
[58] Field of Search .......... 23/253 R, 259; 356/246

[56] References Cited

UNITED STATES PATENTS

| | | | |
|---|---|---|---|
| 3,480,398 | 11/1969 | Hamilton | 23/253 R |
| 3,480,399 | 11/1969 | Hamilton | 23/253 R |
| 3,545,934 | 12/1970 | Dryden et al. | 23/253 R |
| 3,554,705 | 1/1971 | Johnston et al. | 23/253 R |
| 3,582,283 | 1/1971 | Mirasol, Jr. | 23/253 R |
| 3,582,285 | 6/1971 | Hamilton | 23/253 X |

*Primary Examiner*—R.E. Serwin
*Attorney, Agent, or Firm*—Sidney N. Fox

[57] ABSTRACT

A cuvette for use with automatic chemical testing apparatus of the type used for making absorbance measurements of blood serum to which reagents are added to cause chemical changes. The cuvette is disposable, is molded from clear plastic resin as an integral member, has a lower vertically arranged elongate body and an upper funnel-like head portion. The head portion enables positioning of the cuvette in the apparatus where used and the lower portion provides a pair of opposing planar walls through which a beam of radiant energy may be projected and relatively arcuate connecting walls to enable the mixing of the liquids within the cuvette. The configuration enables very little sample to be used in making a test.

13 Claims, 3 Drawing Figures

CUVETTE FOR AUTOMATIC CHEMICAL TESTING APPARATUS

BACKGROUND OF THE INVENTION

The invention is concerned with a cuvette for use with automatic chemical testing apparatus of the type used for making light transmittance measurements of liquid samples such as blood serum, to which various reagents have been added to cause chemical changes. Such apparatus is well-known and usually will process a plurality of liquid samples in small containers or cuvettes. There is a succession of samples which move through the apparatus, these samples being contained in the cuvettes.

Some apparatus will process the samples with different tests in which case all cuvettes may contain serum from a single patient but with different reagents added so that the reactions of the respective tests are different. Some apparatus will process samples from different patients but making the same type of tests for all, in which case the same chemical reagent or reagents will be added to each sample. Some apparatus can perform both types of procedures. The samples have to be identified with respect to the particular source and the particular test, many types of apparatus being capable of handling these problems, but the invention not being concerned with this.

In a typical apparatus, the blood sample is placed in the cuvette, a reagent added, the cuvette stirred and incubated to reach a certain temperature for a certain time while being mechanically stirred, and the resulting liquid mixture or compound interposed between a source of radiant energy and a transducer. The source of radiant energy is usually a beam of light of a certain wave length and the transducer is a photoresponsive device which will produce an electric signal that has a particular relationship with respect to the amount of light which has been absorbed by the mixture in the cuvette. The added reagent and the absorbance characteristic for certain types of chemical tests are known so that the signal from the transducer may be converted into values of certain constituents of the blood of the patient which was the source of the serum. The distance through the liquid sample is generally standardized as 10 millimeters.

The problems which are attempted to be solved by the invention herein may be stated generally as follows:
1. Known cuvettes use large amounts of expensive reagent because they are required to have a certain volume of the resulting mixture through which the beam of light must pass.
2. Known cuvettes have large volumes because of the need to stir the contents and the requirement to accommodate the stirrer.

The invention provides a cuvette which is very small and yet which provides a standard beam transmission distance and accommodates a stirrer. It thus uses less reagent than generally used heretofore for making the same tests.

The form of cuvette which is taught by the invention is simple and economical to manufacture, enables positive location for use, is readily removed and disposed of from the apparatus with which it is used and yet provides efficiency in use of enabling stirring in a small volume which has the standard distance of transmission between walls thereof.

SUMMARY OF THE INVENTION

A cuvette for use with automatic chemical testing apparatus are formed as a molded integral member out of clear synthetic resin. There are two parts comprising an upper head part which is preferably a funnel formation and has means for seating and locating the cuvette properly and a lower part whose walls have a certain configuration that is substantially uniform throughout its vertical extent. The cross sectional configuration of the lower part is generally that of an oval or ellipse which has had its ends on its longer axis flattened. The flattened ends form the planar walls through which the beam of radiant energy will be projected through the liquid sample in the cuvette. The bulging arcuate side walls accommodate the rotation of a stirrer. The total cross sectional area is substantially less than that of an ordinary cuvette used for the same purposes. Thus the total volume of reagent and sample which are accommodated in the cuvette and which will still provide enough for transmission of the beam of light is less than that generally required by other cuvettes to make the same tests.

BRIEF DESCRIPTION OF THE PREFERRED EMBODIMENT

Figure 2:
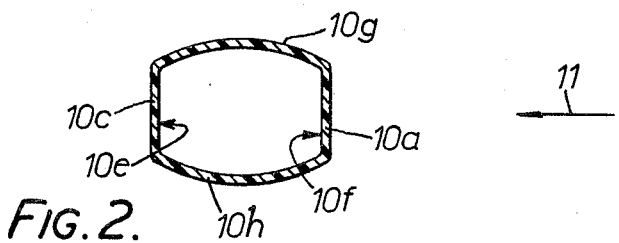
FIG. 2 is a horizontal sectional view taken generally along the line 2—2 of FIG. 1 and in the indicated direction.

The cuvette of the invention is designated generally 10 and has a lower body portion 10a which is to receive the sample and an upper or head portion 10b which is used to position the cuvette 10 properly in the apparatus with which the same is used. The head portion 10b is the liquid sample receiving entrance of the cuvette 10. The configuration of the body portion 10a is generally that of an ellipse or oval which has had its ends on its longer axis flattened as best seen in FIG. 2. This provides the flat vertical planar walls 10c and 10d whose inner facing surfaces 10e and 10f are essentially flat and parallel in order to enable rectilinear substantially distortion-free transmission of a beam of radiant energy such as indicated at 11 therethrough. Obviously the beam 11 will also pass through the solution in the cuvette 10.

The distance between the surfaces 10e and 10f is chosen to be a standard distance which is conventionally used in making absorbance measurements, this being 10 mm. in the practical example. Obviously for other purposes this dimension is a matter of choice.

The connecting walls 10g and 10h are arcuate in a horizontal plane and the distance between them at their furthest parts is substantially less than the distance between the surfaces 10e and 10f but is nevertheless of sufficient degree to accommodate the lateral throw of a stirrer or agitator such as shown at 16. Stirrer 16 may be of nylon, polytetrafluoroethylene, or similar material and is shown here about to enter the cuvette 10 for mixing the solution therein. The dimension between inner surfaces of the walls 10g and 10h was 7.5 mm. in the practical cuvette referred to above. The bottom end of the cuvette is closed off by the wall 10j forming a blind bottom for the cuvette. The walls 10g and 10h which bridge between the vertical planar walls 10c and 10d are generally vertical segments of right cylinders.

Figure 1:
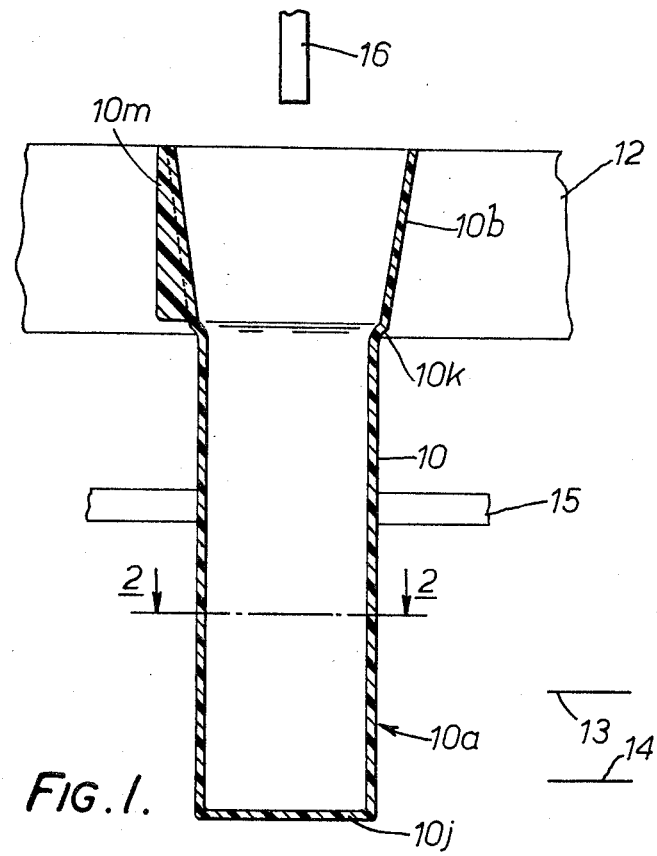
FIG. 1 is a vertical sectional view through a cuvette constructed in accordance with the invention, the environment of use being shown diagrammatically.
Figure 3:
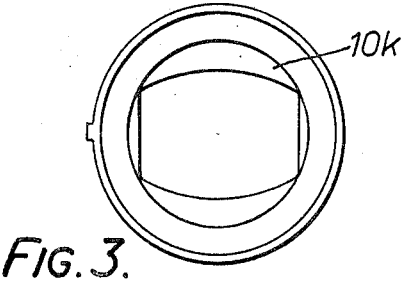
FIG. 3 is a top plan view of the cuvette.

The head portion 10b of the cuvette 10 is frustoconical, of circular cross-section, and is joined to the upper part of the body portion 10a at a shoulder region 10k. This shoulder portion 10k presents a horizontal flat wall of which the upper surface is visible in FIG. 3. When the head portion 10b is placed in a suitable retaining station of a chemical analyzing apparatus, such as for example a carousel indicated at 12 in FIG. 1, the shoulder region 10k provides an accurate vertical locating datum so that the cuvette will extend to a predetermined position below the surface of the carrier 12. Thus, this ensures that a small volume sample held within the bottom of the cuvette 10 will be accurately positioned vertically with respect to the optical examination means which may be located, for example, at a vertical position defined by the lines 13 and 14. The accuracy of such location can be ensured by selecting the diameter of the accommodating passage in the carousel to be between that of the upper and lower ends of frustoconical portion 10b whereby there is an interference fit between the cone and the upper surface of the carrier 12.

Orientation of the cuvette 10 to present the walls 10c and 10d normal to the axis of the beam 11 is effected by means of locating key 10m which is integral with the head portion 10b and which seats in a suitable slot 12a provided in the carousel 12. Preferably there are two such keys which are diametrically located on the exterior of the head 10b. The configuration of the head 10b provides a funnel to facilitate introduction of samples and liquids and the stirrer 16.

In addition to the dimensions of a practical example as given above, the wall thickness of the cuvette was approximately 0.6 mm. and where not molded in split molds, a slight taper could be incorporated to enable removal of the molded article from its mold. The distance from the shoulder portion 10k to the bottom wall 10j was 30 mm. and the height of the head portion 10b was 11.5 mm. The upper circular opening of the funnel was 12 mm. in diameter and the surfaces of the curved walls 10g and 10h had a radius of curvature of about 12.5 mm. which is not critical so long as the stirrer can rotate without interference therewith.

In the installation of the cuvette 10 in the apparatus where used, a plate 15 having an aperture generally congruent with the outer cross section configuration of the cuvette 10 may be spaced below the upper side of the carrier 12. The aperture preferably is only slightly larger than the outer cross-section of the cuvette 12 along the optical axis thereof so as to minimize the possibility of scratching those faces during insertion of said cuvette.

The usual light beam used with this cuvette 10 is about 2 mm. in diameter and is centered about 3 mm. above the bottom wall 10j. The very small volume of the contents of the cuvette 10 provides ample sample for the beam to traverse. This of course is achieved by the configuration of the body 10a. It has been found that with the use of the cuvette of the invention, there is a reduction of about 35 to 45 percent in the normal amount of liquid sample to furnish sufficient sample to enable the tests to be conducted.

There is another advantage of the biconvex cross section of the body 10a and that is that during stirring the configuration has been found to provide a complete mixing without producing stagnant corners in which there might be insufficient intermixing. The mixed sample is thus rendered completely homogeneous.

What it is desired to secure by Letters Patent of the United States is:

1. A cuvette for use with absorbance measuring apparatus adapted to transmit a beam of radiant energy through the cuvette and comprising an integral molded article of transparent synthetic resin and being formed of an upper sample receiving part and a lower liquid retaining part, the lower liquid retaining part having a uniform cross section in a horizontal plane which is generally oval but with the ends flattened, the flattened ends being parallel and forming flat planar walls connected by outwardly convex walls, the distance between the interior faces of the flat planar walls being substantially greater than the distance between the inner surfaces of the convex walls measured at their centers and said lower part having the same configuration along a substantial portion of its vertical extent.

2. The cuvette as claimed in claim 1 in which the juncture between the upper and lower parts defines a shoulder to aid in seating the cuvette in apparatus adapted to receive the same.

3. The cuvette as claimed in claim 1 in which the upper sample receiving part is frusto-conical.

4. The cuvette as claimed in claim 1 in which the upper part has key means adapted to cooperate with suitable structure of apparatus for receiving the same to orient the flat planar walls in a predetermined aspect.

5. The cuvette as claimed in claim 3 in which the upper part has key means adapted to cooperate with suitable structure of apparatus for receiving the same to orient the flat planar walls in a predetermined aspect.

6. The cuvette as claimed in claim 4 in which the key means comprise a pair of vertically arranged keys on opposite sides of the upper part.

7. The cuvette as claimed in claim 2 in which the upper part has key means adapted to cooperate with suitable structure of apparatus for receiving the same to orient the flat planar walls in a predetermined aspect.

8. The combination with an absorbance measuring apparatus which includes a carrier for at least one cuvette, a source of radiant energy for providing a beam arranged horizontally and spaced below the carrier and a transducer responding to the beam, the carrier having means for seating the cuvette in a vertical disposition to receive sample liquid therein between the source and transducer, of a cuvette comprising an integral molded article of synthetic, transparent resin having an upper entrance part and a lower liquid carrying part, the liquid carrying part having a lower blind end, a pair of flat planar vertical walls parallel to one another and being laterally bridged by outwardly bulging arcuate vertical walls that are generally vertical segments of right cylinders such that a cross section on a horizontal plane through said lower liquid carrying part is of the configuration generally of an oval with flattened ends, the cross section of the liquid carrying part being uniform along its length, the distance between the interior surfaces of the planar vertical walls being substantially greater than the distance between the interior surfaces of the outwardly bulging walls at centers, the cuvette having a generally flat bottom end, the blind end being defined at the juncture of the bottom end and side walls, the cuvette having means cooperating with said seating means to dispose the cuvette on the carrier vertically and rotationally such that the beam passes through the cuvette normal to the planar vertical walls just a slight distance above the blind end whereby there will always be sufficient liquid sample in the bottom of the cuvette so that the beam will pass through the sample when being passed through the cuvette.

9. The combination of claim 8 in which the cuvette and seating means include at least one key and slot adapted to engage for providing orientation.

10. The combination of claim 8 in which there is a stirrer which enters the entrance part.

11. The combination of claim 8 in which the entrance part is funnel shaped.

12. The combination of claim 8 in which there is a shoulder formed between the entrance part and the liquid carrying lower part and the carrier includes a horizontal plate for seating the shoulder.

13. The combination of claim 8 in which the cuvette has a pair of diametrically opposite vertical protruding keys and the seating means include a pair of diametrically opposite keyways to receive the keys.

* * * * *